(12) United States Patent
Hell et al.

(10) Patent No.: US 9,891,417 B2
(45) Date of Patent: Feb. 13, 2018

(54) LOCALLY IMAGING A STRUCTURE IN A SAMPLE AT HIGH SPATIAL RESOLUTION

(71) Applicant: Max-Planck-Gesellschaft zur Foerderung der Wissenschaften e.V., Munich (DE)

(72) Inventors: Stefan W. Hell, Goettingen (DE); Fabian Goettfert, Goettingen (DE); Volker Westphal, Hannover (DE)

(73) Assignee: MAX-PLANCK-GESELLSCHAFT ZUR FOERDERUNG DER WISSENSCHAFTEN E.V., Munich (DE)

( * ) Notice: Subject to any disclaimer, the term of this patent is extended or adjusted under 35 U.S.C. 154(b) by 0 days.

(21) Appl. No.: 15/271,888

(22) Filed: Sep. 21, 2016

(65) Prior Publication Data
US 2017/0082844 A1   Mar. 23, 2017

(30) Foreign Application Priority Data

Sep. 22, 2015 (DE) .................. 10 2015 116 023
Mar. 7, 2016 (DE) .................. 10 2016 104 100

(51) Int. Cl.
*F21V 9/16* (2006.01)
*G02B 21/00* (2006.01)
(Continued)

(52) U.S. Cl.
CPC ..... *G02B 21/0036* (2013.01); *G01N 21/6458* (2013.01); *G02B 21/0076* (2013.01); *G02B 21/16* (2013.01); *G02B 27/58* (2013.01)

(58) Field of Classification Search
CPC ........... G01N 21/6428; G01N 21/6458; G01N 21/64; G01N 21/6408; G01N 2021/6421
See application file for complete search history.

(56) References Cited

U.S. PATENT DOCUMENTS 6,903,347 B2 * 6/2005 Baer .................. G02B 21/0056
250/458.1
7,646,481 B2   1/2010 Dyba
(Continued)

FOREIGN PATENT DOCUMENTS

DE   10 2005 027 896 A1   12/2006
DE   10 2006 009 833 B4   1/2009
(Continued)

OTHER PUBLICATIONS

Engelhardt "Quadscanner for High Resolution Scanning Microscopes" German Cancer Research Center, p. 1-2, Oct. 2012.*
(Continued)

*Primary Examiner* — David Porta
*Assistant Examiner* — Mamadou Faye
(74) *Attorney, Agent, or Firm* — Thomas | Horstemeyer, LLP

(57) ABSTRACT

For high spatial resolution imaging a structure in a sample, the structure being marked with luminescence markers, light that has an effect on the emission of luminescence light by the luminescence markers is directed onto the sample with an intensity distribution having a zero point and intensity maxima neighboring the zero point in at least one direction. A scan area which is a part of the sample is scanned with the zero point. Luminescence light emitted out of a local area including the zero point is registered and assigned to the respective location of the zero point in the sample. Dimensions of the scan area, in at least one direction in which the intensity maxima are neighboring the zero point, are limited such that they are not larger than 75% of a distance of the intensity maxima in the at least one direction.

27 Claims, 10 Drawing Sheets

(51) Int. Cl.
*G01N 21/64* (2006.01)
*G02B 21/16* (2006.01)
*G02B 27/58* (2006.01)

(56) References Cited

U.S. PATENT DOCUMENTS

| | | |
|---|---|---|
| 7,679,741 B2 | 3/2010 | Dyba |
| 7,719,679 B2 | 5/2010 | Hell |
| 7,903,247 B2 | 3/2011 | Dyba |
| 8,399,857 B2 * | 3/2013 | Lippert .............. G01N 21/6458 250/461.1 |
| 8,520,280 B2 | 8/2013 | Engelhardt |
| 8,705,172 B2 | 4/2014 | Kleppe |
| 9,024,279 B2 | 5/2015 | Hell |
| 9,267,888 B2 | 2/2016 | Hell |
| 9,377,406 B2 | 6/2016 | Hell |
| 2012/0104279 A1 | 5/2012 | Reuss |
| 2013/0201558 A1 | 8/2013 | Baer |
| 2014/0042340 A1 * | 2/2014 | Hell ..................... G01N 21/645 250/459.1 |
| 2014/0097358 A1 | 4/2014 | Hell |
| 2014/0340482 A1 | 11/2014 | Kanarowski |
| 2015/0308955 A1 * | 10/2015 | Hell ................... G01N 21/6428 250/459.1 |
| 2016/0246042 A1 | 8/2016 | Enderlein |
| 2017/0031145 A1 | 2/2017 | Takiguchi |

FOREIGN PATENT DOCUMENTS

| | | |
|---|---|---|
| DE | 10 2011 051 086 A1 | 12/2012 |
| DE | 10 2013 100 174 A1 | 7/2014 |
| DE | 10 2013 017 468 A1 | 3/2015 |
| DE | 10 2013 114 860 B3 | 5/2015 |
| EP | 2 317 362 A1 | 10/2010 |
| JP | 2015 200693 A | 11/2015 |
| WO | 2010/069987 A1 | 6/2010 |
| WO | 2011/131591 A1 | 10/2011 |
| WO | 2014/108455 A1 | 7/2014 |

OTHER PUBLICATIONS

Li D et al.: Extended-resolution structured illumination imaging of endocytic and cytoskeletal dynamics, Science Aug. 28, 2015; 349(6251).

R A Hoebe et al.: Controlled light-exposure microscopy reduces photobleaching and phototoxicity in fluorescence live-cell imaging, Nature Biotechnology, vol. 25, No. 2, Feb. 2007, pp. 249 to 253.

T. Staudt et al.: Far-field optical nanoscopy with reduced number of state transition cycles, Optics Express vol. 19, No. 5, Mar. 14, 2011, pp. 5644 to 5657.

U.S. Appl. No. 15/189,300, filed Jun. 22, 2016, entitled "High-Resolution Fluorescence Microscopy Using a Structured Beam of Excitation Light". Copy attached.

International Search Report in related PCT Application No. PCT/EP2017/055360, dated Jun. 29, 2017.

* cited by examiner (a)            (b)

LOCALLY IMAGING A STRUCTURE IN A SAMPLE AT HIGH SPATIAL RESOLUTION

CROSS REFERENCE TO RELATED APPLICATIONS

This application claims priority to German Patent Application No. DE 10 2015 116 023.4 filed on Sep. 22, 2015, and to German Patent Application No. DE 10 2016 104 100.9, filed on Mar. 7, 2016.

FIELD

The present disclosure relates to a method of spatial high resolution imaging a structure in a sample, the structure being marked with luminescence markers. Further, this disclosure relates to a scanning luminescence light microscope for carrying out this method.

The invention belongs to the field of high resolution scanning luminescence light microscopy in which measures are taken which allow for assigning luminescence light emitted out of the respective sample to a location in the sample at a higher spatial resolution than the diffraction barrier at the wavelength of the luminescence light and at the wavelength of any excitation light by which the luminescence markers are excited for the emission of luminescence light in a spatially limited area. Often, the luminescence markers are fluorescence markers that emit fluorescence light as luminescence light after excitation by excitation light. Then, one refers to fluorescence microscopy.

BACKGROUND

In known methods of and scanning luminescence light microscopes for spatial high resolution imaging a structure in a sample, the structure being marked with luminescence markers, light that has an effect on the emission of luminescence light by the luminescence markers is directed onto the sample with an intensity distribution that has a zero point and intensity maxima neighboring the zero point for increasing the spatial resolution. Often, this light is luminescence inhibition light inhibiting the emission of luminescence light by all those luminescence markers which are outside the zero point. The luminescence light emitted out of the sample may thus be assigned to the location of the zero point in the sample, as only luminescence markers located there are able to emit luminescence light.

In STED fluorescence microscopy, for instance, fluorescence markers previously excited by means of excitation light are de-excited again by means of stimulation light as fluorescence inhibiting light, except of those fluorescence markers in the area of the zero point, so that only the fluorescence markers located in the area of the zero point may have emitted the fluorescence light measured afterwards. This fluorescence light may thus be assigned to the location of the zero point in the sample. The spatial distribution of the fluorescence marker within the sample is determined by scanning the sample with the zero point. In this way, the shape and the spatial distribution of a structure in the sample, which is marked with the fluorescence markers, may be imaged.

In GSD fluorescence microscopy, the fluorescence inhibiting light transfers those fluorescence markers outside the area of the zero point into an electronic dark state so that they are no longer excitable for emission of fluorescence light by means of excitation light.

In RESOLFT fluorescence microscopy, fluorescence inhibiting light is used which transfers photochromic fluorescence markers out of a fluorescent state into a non-fluorescent state, except of those fluorescence markers in the area of the zero point. When the fluorescence markers are afterwards subjected to excitation light, only those fluorescence markers in the area of the zero point of the intensity distribution of the fluorescence inhibiting light are excited for the emission of fluorescence light by the excitation light. Thus, the fluorescence light emitted by the fluorescence markers in the sample may also be assigned to the location of the zero point of the intensity distribution of the fluorescence inhibiting light in the sample, here.

In all methods of high spatial resolution scanning luminescence light microscopy described up to here, there is an essential danger of temporarily or even permanently bleaching the luminescence markers in the respective sample, i.e. of deactivating them so that they can no longer emit luminescence light. This danger is due to the fact that the intensity of the luminescence inhibition light has to be very high in order to stop all luminescence markers outside the area of the zero point from the emission of luminescence light and to also strongly spatially delimit the dimensions of the area of the zero point out of which the luminescence markers may still emit luminescence light. With this high intensity, the luminescence inhibiting light already stresses the luminescence markers in the sample when the area of the zero point of the luminescence inhibiting light gets closer to the luminescence markers, i.e. already before they get into the area of the zero point for a first time and thus prior to luminescence light emitted by them being registered for the first time. This may have the consequence that luminescence markers having a tending to bleach may not be used in the described methods at all or may at least not be used with high intensities of the luminescence inhibiting light as they are desirable for maximizing the spatial resolution.

Several approaches were pursued to avoid the described problems of a temporal and particularly of a permanent bleaching in high resolution scanning luminescence light microscopy. German patent application publication DE 10 2005 027 896 A1 and U.S. Pat. No. 7,719,679 B2 belonging to the same patent family teach to apply stimulation light to a sample in STED fluorescence microscopy in pulses at comparatively long temporal intervals or while very quickly scanning the respective sample with a zero point of an intensity distribution of the stimulation light so that the same areas of the sample are only subjected to the high intensity of the fluorescence inhibiting light in maxima neighboring the zero point at an optimized temporal repetition interval. In this way, the intensity of fluorescence light obtainable from the sample is increased, as the rate at which the fluorescence markers get into a permanent or only slowly decaying dark state out of an excited intermediate state by means of further excitation by the stimulation light is reduced considerably. In other words, by means of the comparatively long repetition interval at which each individual area of the sample is subjected to the intensity distribution of the fluorescence inhibiting light, the overall amount of fluorescence light obtainable from the entire sample within a certain period of time is maximized. This procedure also reduces the tendency of the fluorescence markers to bleach as a higher population of excited states out of which a photochemical destruction of the fluorescence markers may occur is avoided.

For carrying out high spatial resolution fluorescence microscopy even with fluorescence markers tending to bleach, German patent application publication DE 10 2011

051 086 A1 and US patent application publication US 2014/0097358 A1 belonging to the same patent family teach to adjust scanning conditions with regard to each other, which—besides a scanning speed at which the sample is scanned and a light intensity of an intensity distribution of fluorescence inhibiting light—include properties and a concentration of the fluorescence markers within the sample, in such a way that the fluorescence light is emitted out of the area of a zero point of the intensity distribution of the fluorescence inhibiting light as individually detectable photons. An image of a structure in the sample, which is marked with the fluorescence markers, is then composed of the locations of the zero point, to which the detected photons are assigned during several repetitions of scanning the sample with the zero point. In this way, the probability of bleaching the fluorescence markers, before they are reached with the zero point and thus measured for the first time, is reduced. This is due to the fact that the probability of bleaching is correlated with the intensity of the fluorescence light obtained from the individual fluorescence markers. As the fluorescence light is minimized to individual photons, the danger of bleaching is also minimized. Generally, however, in the method known from DE 10 2011 051 086 A1 and US 2014/0097358 A1 the zero point of the fluorescence inhibiting light still only reaches the individual fluorescence markers after they have previously been subjected to the high intensities in the area of the intensity maxima of the fluorescence inhibiting light neighboring the zero point.

For also being able to use substances liable to bleaching in high spatial resolution scanning luminescence light microscopy, it is known from International patent application publication WO 2011/131591 A1 and U.S. Pat. No. 9,024,279 B2 belonging to the same patent family to move a measurement front across the sample in which a structure of interest is marked with luminescence markers. In the measurement front, the intensities of optical signals increase over a depth of the measurement front which is smaller than the diffraction barrier at the wavelength of the optical signals in such a way that a portion of the luminescence markers which emit luminescence light is increased starting from non-existing and then reduced back to non-existing again by first transferring the luminescence markers into a luminescent state and by then transferring the luminescence markers into a non-luminescent state. The luminescence light out of the area of the measurement front is registered and assigned to the respective position of the measurement front in the sample. The assignment of the luminescence light to a certain location along the measurement front may also take place at a spatial resolution beyond the diffraction barrier by, for example, assigning the registered photons to a single luminescence marker in a same way as in a light microscopic method known as GSDIM.

An option of increasing the speed of imaging a structure of interest of a sample in scanning luminescence light microscopy is to scan the sample with a plurality of zero points of luminescence inhibiting light in parallel. Here, the luminescence light emitted out of the sample is separately assigned to the individual zero points of the luminescence inhibiting light. From German patent DE 10 2006 009 833 B4 and U.S. Pat. No. 7,903,247 B2 and U.S. Pat. No. 7,646,481 B2 belonging to the same patent family it is known to form an intensity distribution of luminescence inhibiting light with a grid of zero points in that two orthogonal line patterns of luminescence inhibiting light are superimposed within the sample. An interference between the light of the two line patterns is avoided so that their intensity distributions simply add up. The desired zero points of the intensity distribution of the luminescence inhibiting light remain at the crossing points of the line-shaped zero points of both line gratings and they are delimited by neighboring intensity maxima of the luminescence inhibiting light. To completely scan the sample in the area of the grid-shaped arrangement of the zero points, it is sufficient to shift each zero point over the distances to its nearest neighbors in the two directions of the two line patterns. Again, most of the luminescence markers in the sample are subjected to high light intensities of the luminescence inhibiting light before one of the zero points reaches them so that they are registered for the first time. Thus, the luminescence markers have to be selected such that they withstand these high light intensities without bleaching.

Li D et al.: Extended-resolution structured illumination imaging of endocytic and cytoskeletal dynamics, Science 2015 Aug. 28; 349(6251) disclose a method of spatial high resolution imaging a structure in a sample, the structure being marked with activatable fluorescence markers, wherein the sample is successively scanned with coinciding line- or plane-shaped zero points of light intensity distributions of fluorescence activation light and fluorescence inhibiting light in different directions, and wherein the fluorescence light emitted by the sample is registered with a camera. By means of evaluating the registered light intensities, an image of the structure of interest in the sample may be reconstructed whose spatial resolution is increased due to narrowing down the coinciding zero points of the fluorescence activation light and the fluorescence excitation light out of which no fluorescence light is emitted from the sample. Further, in this known method, the zero points of the fluorescence activation light and of the fluorescence excitation light which simultaneously acts as fluorescence deactivation light are delimited by intensity maxima of the fluorescence activation light and the fluorescence excitation light. All luminescence markers in the sample are subjected to the high intensities of the fluorescence activation light and the fluorescence excitation light in the area of these intensity maxima, before they get into the area of the coinciding zero points of the fluorescence activation light and the fluorescence excitation light. Thus, the risk of bleaching the fluorescence markers, before they contribute to the relevant measurement signal, is very high in this known method as well.

International patent application publication WO 2014/108455 A1 and U.S. Pat. No. 9,267,888 B2 belonging to the same patent family disclose a method of high spatial resolution imaging a structure in a sample, the structure being marked with luminescence markers, in which the sample, like in STED fluorescence microscopy, is subjected to excitation light and to stimulation light as luminescence inhibiting light to reduce the area of the sample to which fluorescence light emitted out of the sample and detected may be assigned to the area of a zero point of the stimulation light. For protecting the luminescence markers against high intensities of the stimulation light in the area of its maxima neighboring the zero point, the sample is additionally subjected to excitation inhibiting light whose intensity distribution has a local minimum which coincides with the zero point of the stimulation light. This excitation inhibiting light may particularly be switch off light which switches switchable luminescence markers located outside the minimum of the excitation inhibiting light into an inactive state in which they are not excitable for emission of fluorescence light by means of the excitation light. Particularly, the luminescence markers may be switchable fluorescence dyes as they are used in high spatial resolution RESOLFT fluorescence microscopy. In the method known from WO 2014/108455 A1 and U.S. Pat. No. 9,267,888 B2, however, the switchability of the luminescence markers is primarily not used for increasing the spatial resolution but for protecting the luminescence markers against bleaching due to the high intensities of the stimulation light.

R A Hoebe et al.: Controlled light-exposure microscopy reduces photobleaching and phototoxicity in fluorescence live-cell imaging, Nature Biotechnology, Volume 25, No. 2, February 2007, pages 249 to 253 disclose a method of confocal fluorescence microscopy in which a sample is scanned with focused excitation light to image a structure in the sample, the structure being marked with luminescence markers. Here, the excitation light is switched off in each position of the focused excitation light within the sample as soon as a number of photons which are emitted by the excited luminescence markers in the sample and registered by a detector reach an upper threshold corresponding to a desired signal-to-noise ratio. The excitation light is also switched off if the number of the emitted and registered photons does not reach a lower threshold within a predetermined part of the maximum pixel dwell time, because this indicates that no relevant concentration of luminescence markers is found in the sample at the respective position of the focused excitation light. In this way, the load of the sample by excitation light is considerably reduced as compared to subjecting the sample with the same amount of light in each position.

T. Staudt et al.: Far-field optical nanoscopy with reduced number of state transition cycles, Optics Express Vol. 19, No. 6, 14 Mar. 2011, pages 5644 to 5657 disclose a method called RESCue-STED which transfers the method described by R A Hoebe et al. for confocal fluorescence microscopy to STED fluorescence microscopy. Here, the sample is only subjected to the high intensities of the stimulation light as long as necessary or suitable.

There still is a need of methods of high spatial resolution imaging a structure in a sample, the structure being marked with luminescence markers, and of a scanning luminescence light microscope for executing such methods in which the load to the luminescence markers in the sample by high light intensities is generally reduced so that even luminescence markers which are sensitive to high light intensities may be used and/or a structure in the respective sample may be imaged repeatedly to, for example, monitor changes of the structure during the course of a biological process.

SUMMARY OF THE INVENTION

The present invention provides a method of high resolution imaging a structure in a sample, the structure being marked with luminescence markers. The method comprises directing light that has an effect on the emission of luminescence light by the luminescence markers onto the sample with an intensity distribution which has a zero point and intensity maxima neighboring the zero point in at least one direction; scanning a scan area with the zero point, the scan area being a part of the sample; while scanning the scan area registering luminescence light emitted out of a local area including the zero point in the sample; and assigning the registered luminescence light to a respective location of the zero point in the sample. Dimensions of the scan area, in the at least one direction in which the intensity maxima are neighboring the zero point in the sample, are limited such that they are not larger than 75% of a distance of the intensity maxima in the at least one direction.

The present invention also provides a further method of high spatial resolution imaging a structure in a sample, the structure being marked with luminescence markers. This method comprises directing light that has an effect on the emission of luminescence light by the luminescence markers onto the sample at an intensity distribution which has a zero point and intensity maxima neighboring the zero point in at least one direction; scanning a scan area with the zero point, the scan area being a part of the sample; while scanning the scan area registering luminescence light emitted out of a local area including the zero point in the sample; and assigning the registered luminescence light to a respective location of the zero point in the sample. Here, the scan area is scanned with the zero point starting at a center point and with increasing distance to the center point in the at least one direction.

Further, the present invention provides a scanning luminescence light microscope comprising a light source configured to provide light; a light shaper configured to direct the light onto a sample with an intensity distribution having a zero point and intensity maxima neighboring the zero point; a scanner configured to scan a scan area with the zero point, the scan area being a partial area of the sample; a detector configured to register luminescence light emitted out of the area of the zero point; and a controller programmed with software implementing at least one of the above methods.

Other features and advantages of the present invention will become apparent to one with skill in the art upon examination of the following drawings and the detailed description. It is intended that all such additional features and advantages be included herein within the scope of the present invention, as defined by the claims.

SHORT DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

FIG. 1 schematically shows intensity distributions of excitation light and fluorescence inhibiting light as an example of light which has an effect on the emission of luminescence light by luminescence markers in the sample, and the resulting effective excitation of fluorescence markers in a sample for emission of fluorescence light.

Figure 6:
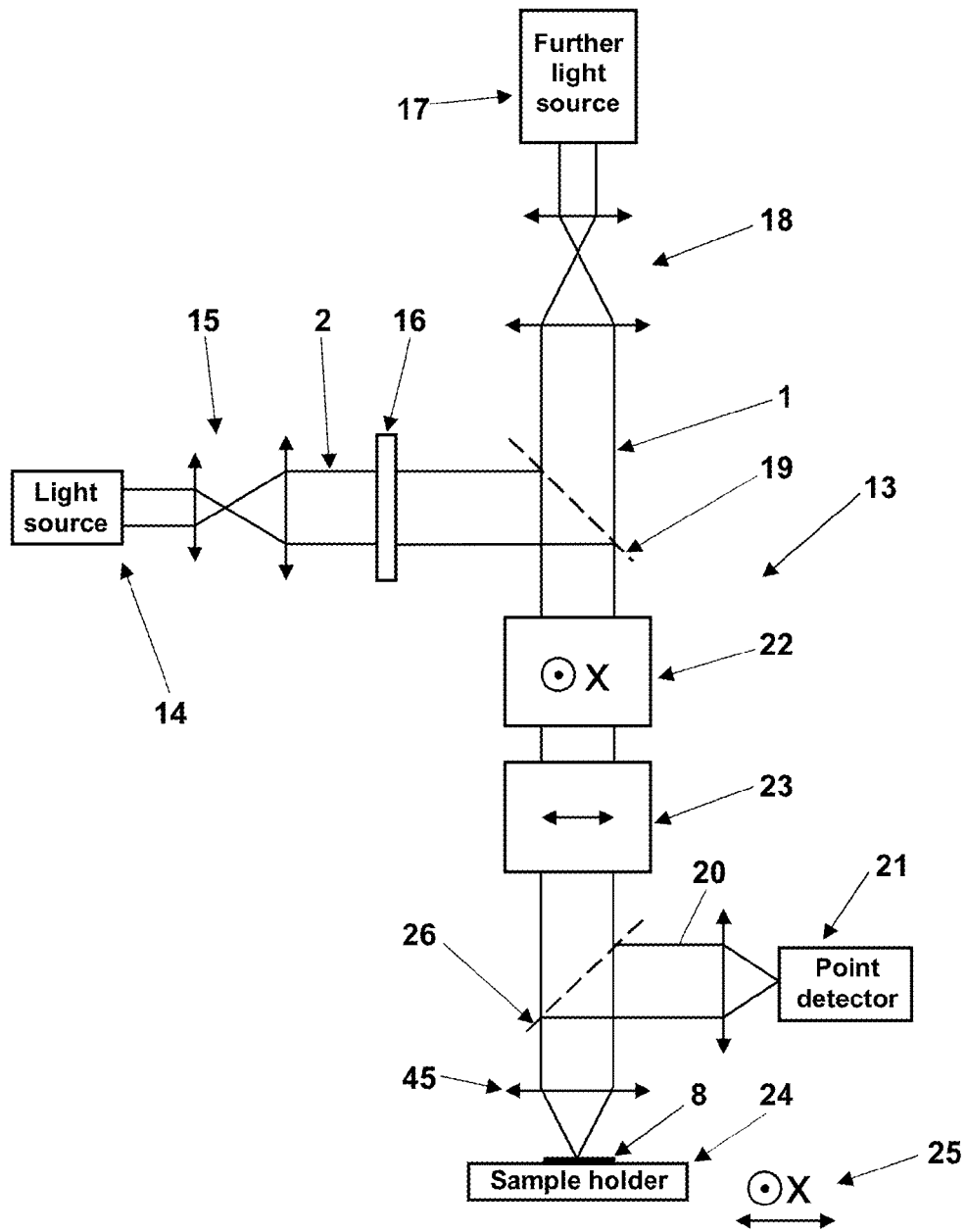

FIG. 6 schematically illustrates a fluorescence microscope as an example of a scanning luminescence light microscope according to the invention.

Figure 7:
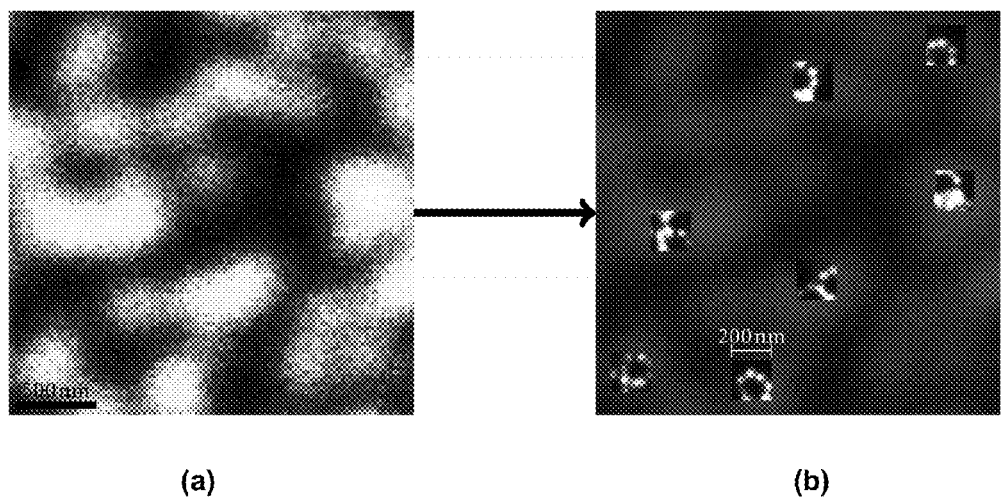

FIG. 7 shows (a) a confocal image of a sample taken upfront, and (b) a partial image of the sample taken according to the present invention, after individual scan areas of the sample have been selected based on the confocal image.

Figure 8:
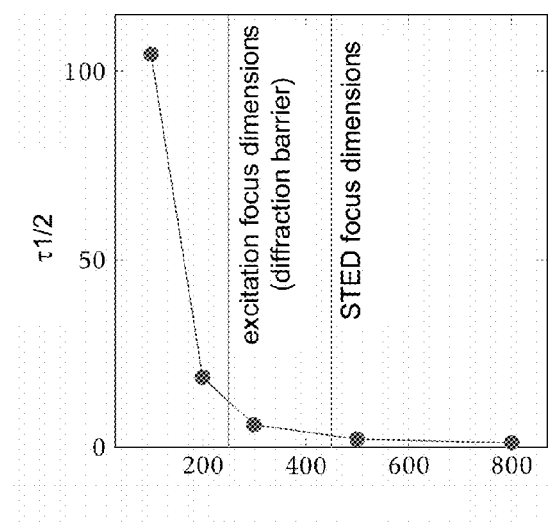

FIG. 8 shows the dependency between the number of the images which may successively be taken of a scan area of the sample and the dimensions of the scan area.

Figure 9:
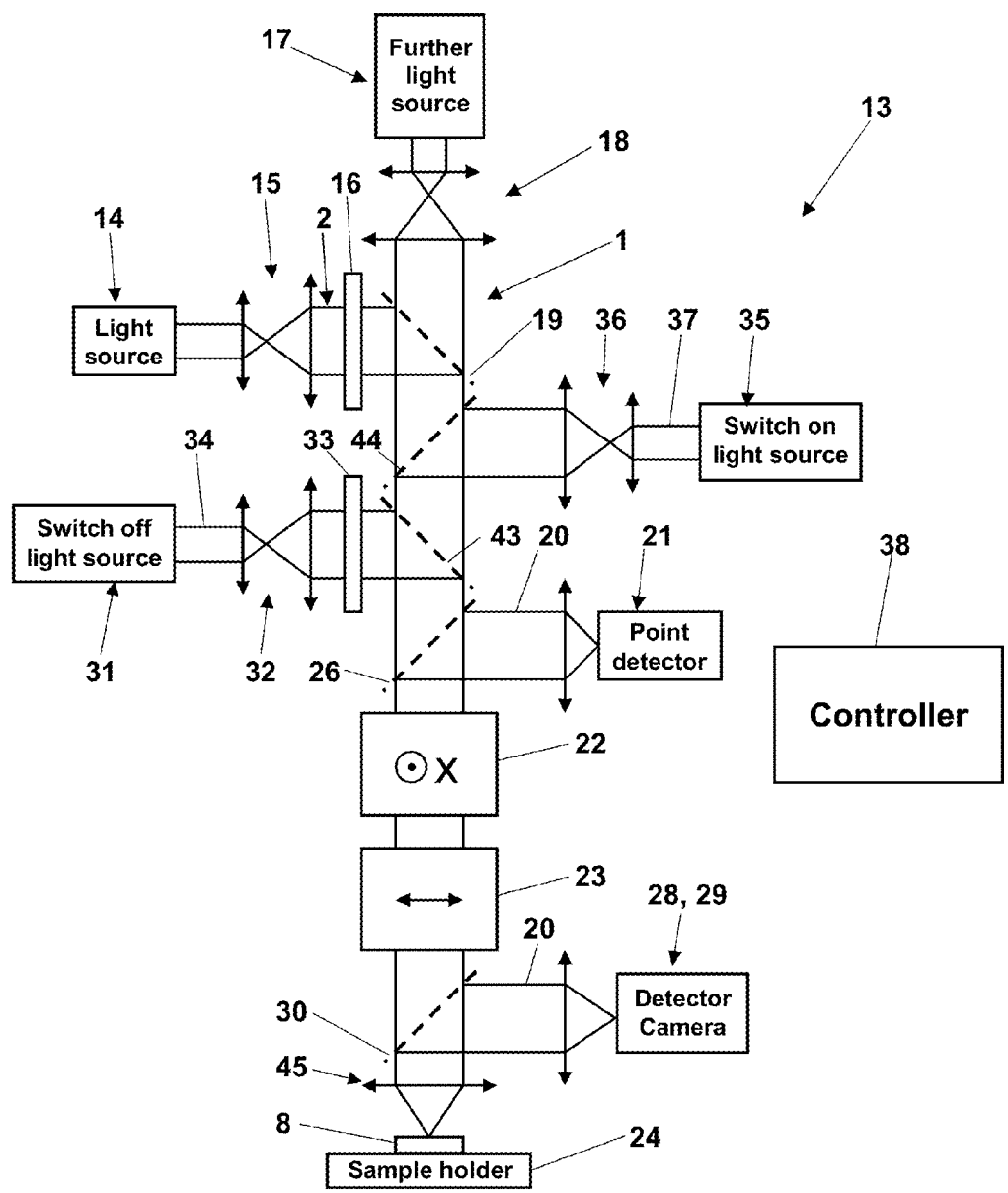

FIG. 9 schematically shows another fluorescence microscope than in FIG. 6 as a further embodiment example of a scanning luminescence microscope according to the invention.

Figure 10:
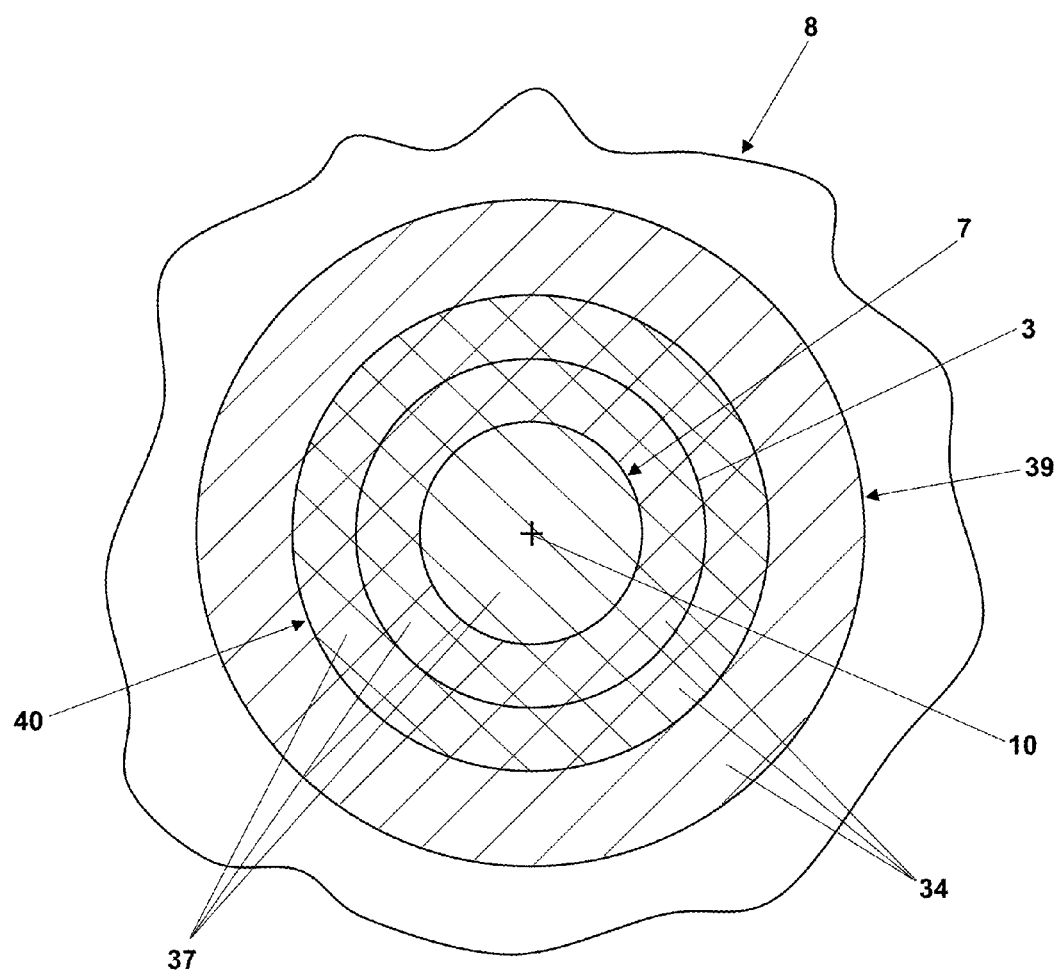

FIG. 10 is a schematic drawing of a scan area of a sample to be scanned with additional depiction of a neighboring area in which switch off light is directed onto the sample by means of the scanning fluorescence microscope of FIG. 9.

Figure 11:
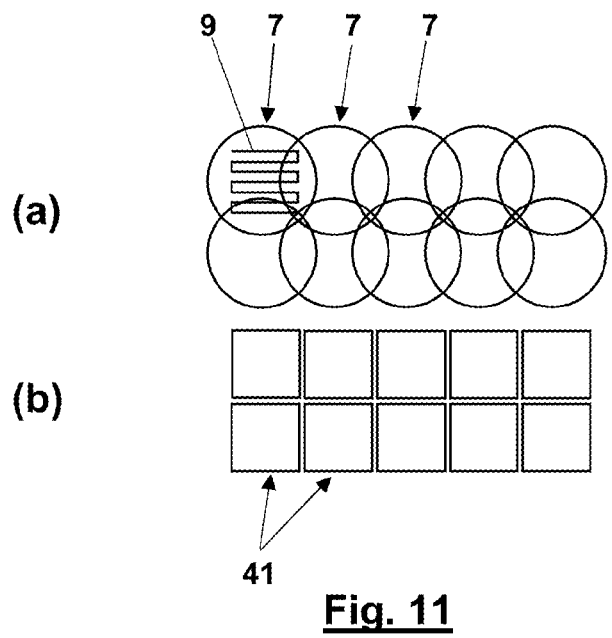

FIG. 11 illustrates an arrangement of several scan areas in the sample, which are to be scanned according to FIG. 10, to scan the sample with the scan areas.

Figure 12:
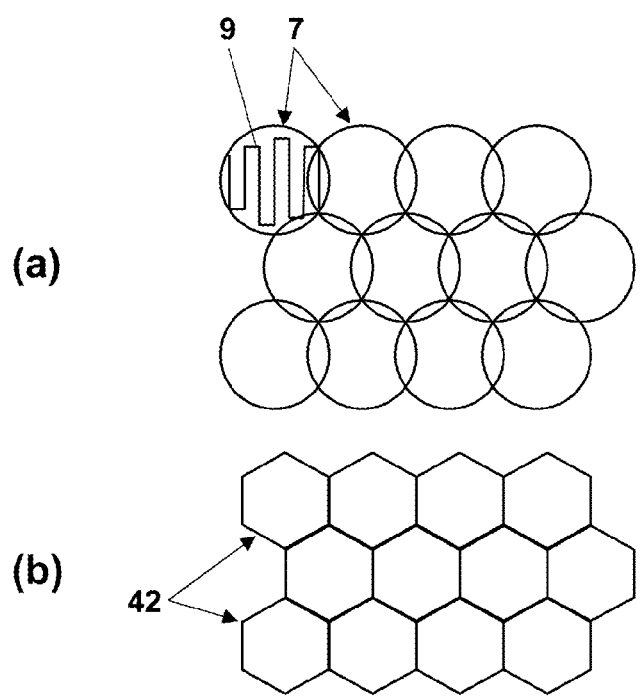

FIG. 12 illustrates another arrangement of scan areas in the sample.

Figure 13:
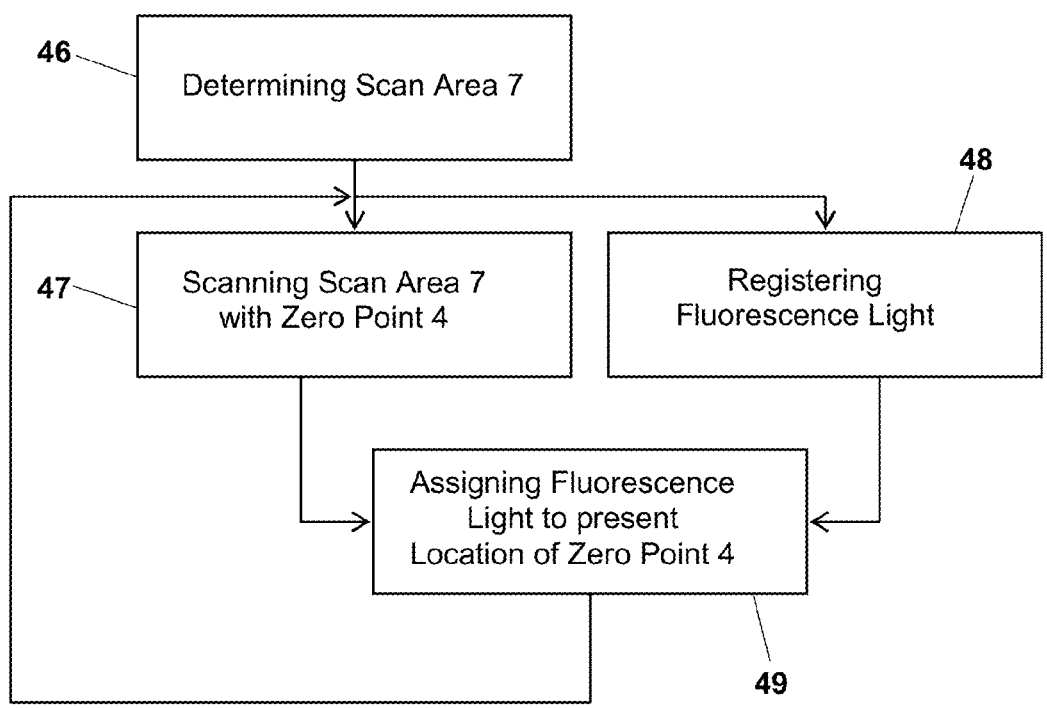
Figure 14:
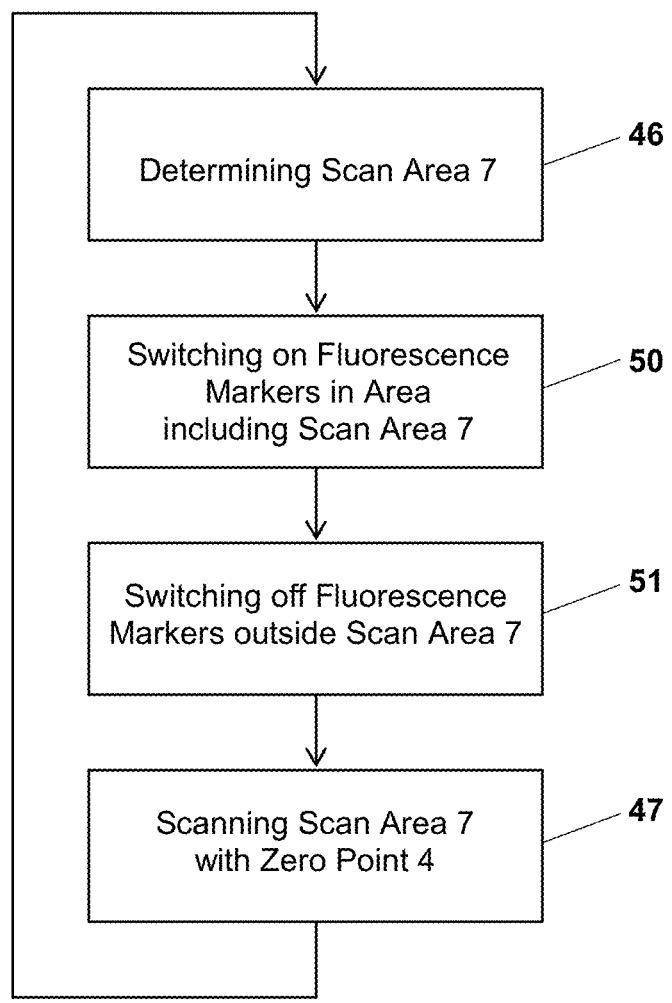

FIG. 13 is a block diagram of one embodiment of the method according to the present invention; and FIG. 14 is a block diagram of another embodiment of the method according to the present invention.

DETAILED DESCRIPTION

In a method according to the present invention of spatial high resolution imaging a structure in a sample, the structure being marked with luminescence markers, light that has an effect on the emission of fluorescence light by the luminescence markers is directed onto the sample with an intensity distribution having a zero point and intensity maxima neighboring the zero point. A scan area which is a partial area of the sample is scanned with the zero point, and luminescence light emitted out of a local area including the zero point is registered and assigned to the respective location at which the zero point was located in the sample when the luminescence light was registered. Dimensions of the scan area are, in at least one direction and particularly in every direction in which the intensity maxima are neighboring the zero point, limited to not more than 75% of a distance of the intensity maxima in the respective direction.

In so far as luminescence markers are mentioned here, they may particularly be fluorescence markers. However, other luminescence markers may also be used whose luminescence properties may, for example, be based on chemiluminescence or electroluminescence. This includes that the excitation of the luminescence markers for the emission luminescence light is not limited to particular mechanisms in the method according to the present invention. Often, however, the excitation of the luminescence markers for the emission of luminescence light will be by excitation light.

The light that has an effect on the emission of luminescence light by the luminescence markers may be luminescence inhibiting light which inhibits the emission of luminescence light by the luminescence markers in that it for example transfers the luminescence markers into a dark state or de-excites excited luminescence markers by stimulated emission and thus inhibits them to emit luminescence light. Further, the light that has an effect on the emission of luminescence light by the luminescence markers may be light which transfers the luminescence markers out of a non-luminescent state into a further non-luminescent state in which they are particularly well protected against bleaching. Further, the light that has an effect on the emission of luminescence light by the luminescence markers may be light which only has such an effect on the emission of luminescence light by the luminescence markers that this emission only occurs out of the area of the zero point of the intensity distribution of the light, if it is combined with other light.

In another embodiment, the light that has an effect on the emission of luminescence light by the luminescence markers is luminescence enabling light which enables the emission of luminescence light by the luminescence markers in that it, for example, excites the luminescence markers for luminescence or transfers the luminescence markers out of a dark state into an excitable state.

The zero point of the intensity distribution of the light that has an effect on the emission of luminescence light by the luminescence markers is at least a local intensity minimum of the intensity distribution of the light. Often, it will be an intensity minimum in which the intensity of the light essentially drops to zero. In an ideal case, the intensity of the light in fact drops to zero in the center of the zero point. This, however, is no imperative requirement. If the light is luminescence inhibiting light, for example, it is sufficient if the intensity of the luminescence inhibiting light is so low in the area of the zero point that there is no or at least no essential, i.e. at least no predominant inhibition of the luminescence of the luminescence markers. The zero point is then delimited by the areas in which the luminescence inhibiting light at least essentially inhibits the emission of luminescence light by the luminescence markers. Everything between these areas in which the luminescence inhibiting light at least essentially inhibits the emission of luminescence light by the luminescence markers is called "zero point" or "area of the zero point", here.

If the intensity maxima neighboring the zero point of the intensity distribution of the light that has an effect on the emission of luminescence light by the luminescence markers are referenced in plural here, this shall not exclude the case in which the zero point is enclosed by an intensity maximum extending as a ring around the zero point. In each virtual section through the intensity distribution of the light that has an effect on the emission of luminescence light, such a ring-shaped intensity maximum appears in the form of two intensity maxima neighboring the zero point on both sides in the section.

The intensity maxima may be neighboring the zero point in one, two or three directions. Thus, the zero point may be plane-shaped, line-shaped or point-shaped. The zero point may intersect a two- or one-dimensional sample in such a way that even a line-shaped or point-shaped zero point is delimited by the intensity maxima in all directions of main extension of the sample. Further, the scan area may successively be scanned with a zero point which is not delimited by the intensity maxima in all directions of main extension of the sample with different orientations of the zero point to maximize the spatial resolution in imaging in all directions of main extension of the sample. The physical dimensions of the scan area are limited in at least one direction, preferably in all directions in which the intensity maxima are neighboring the zero point in the sample.

The intensity maxima neighboring the zero point in the sample are often of a much higher light intensity than those areas of the intensity distribution of the light that has an effect on the emission of luminescence light by the luminescence marker which are directly delimiting the area of the zero point and in which the light already has the desired effect on the emission of luminescence light by the luminescence markers in that it, for example, inhibits this emission. The very high intensities in the intensity maxima are a consequence of the overall high intensity of the light which, on the other hand, is a precondition for that the area of the zero point in which the light has at least essentially no effect on the emission of luminescence light by the luminescence markers is strongly spatially delimited. As a consequence, there are intermediate areas between those areas of the light intensity distribution directly delimiting the area of the zero point and the intensity maxima of the intensity distribution in which the light intensity remains far below the light intensity within the intensity maxima. These intermediate areas are purposefully used in the method according to the invention in that the dimensions of the scan area do not exceed 75% of the distance of the intensity maxima in the respective direction. If the dimension of the scanned area remains smaller than 50% of the distance of the intensity maxima in the respective direction, no point of the scan area is subjected to the full intensity of the light intensity maxima. But even with a limit of 75% of the distance there is a significant limitation to the average intensity of the light that has an effect on the emission of luminescence light to which the scan area is subjected to. It is to be understood that the average intensity of the light to which the scan area is subjected to gets the smaller the more its dimensions remain smaller than the distance of the intensity maxima in the respective direction. From an absolute point of view, the dimensions of the scan area in the respective direction between the intensity maxima may be 300 nm at maximum. Preferably, the dimensions in the respective direction are 200 nm at maximum, and more preferably they are about 100 nm. These absolute figures are related to wavelengths of the luminescence light, of the light that has an effect on the emission of luminescence light by the luminescence markers and/or of possible excitation light which are all in the visible range.

The scan area may be a partial area of the sample which is the only partial area of the sample scanned when executing the method according to the present invention and which, correspondingly, is to be directed to an area of interest in the sample, i.e. to a detail of interest of the structure marked with the luminescence markers in the sample.

The invention purposefully accepts that the scanned and thus imaged partial area of the sample remains small. Often, the scan area extends over a distance of the order of magnitude of the diffraction barrier at the wavelength of the light that has an effect on the emission of the luminescence light by the luminescence markers. On the other hand, due to the essential reduction of the average light intensities to which the scan area is subjected, it is possible to successfully use even luminescence markers with a strong tendency to bleaching or to scan the scan area in the sample repeatedly with the zero point of the light intensity distribution.

The option of scanning the scan area in the sample repeatedly at a high repetition rate with the zero point of the intensity distribution also enables to temporarily resolve dynamic processes in the structure of interest in the sample. As the luminescence markers in the sample, due to the method according to the invention, have a particularly low tendency to bleach so that a particular high number of photons is obtained from each individual fluorescence marker in the scan area, particularly many images of the scan area of the sample may be taken, and thus even long time variations of the structure of interest in the sample may be observed. As a rule, the scan area is scanned in not more than 100×100=10,000 image points. This is possible within a few milliseconds. Thus, image frequencies of 100 Hz and more can be realized.

Advantageously, in each direction in which the intensity maxima are neighboring the zero point in the sample, the dimensions of the scan area are not larger than 45%, 25% or even 10% of the distance of the intensity maxima in the respective direction. With regard to the intensity of the light that has an effect on the emission of luminescence light by the luminescence markers, it is advantageous if the dimensions of the partial area of the sample, in each direction in which the intensity maxima are neighboring the zero point in the sample, are not larger than the distance over which the intensity of the light starting at the zero point increases in the respective direction up to 50%, 25%, 10% or 5% of the intensity of the light in the neighboring intensity maxima. Correspondingly, the maximum load of the luminescence markers in the scanned area is limited to 50%, 25%, 10% or 5% of the intensity of the light in the neighboring intensity maxima.

The same findings on which the embodiment of the present invention described up to here is based are also used in another embodiment of the method according of the invention in which a scan area of the sample is scanned starting at a center point and with increasing distance to this center point. As long as the distance to the center point remains smaller than 75% of the distance of the intensity maxima neighboring the zero point in the sample in the same direction, the average load by the light having an effect on the emission of fluorescence light by the fluorescence markers on the scan area remains small as compared to known scanning luminescence light microscopy methods. In any case, the luminescence markers located close to the center point are registered with regard to their location in the sample prior to being subjected to higher intensities of the light that has an effect on the emission of luminescence light. Thus, with luminescence markers tending to bleach, the relative intensity of the registered luminescence light may decrease with increasing distance to the center point, particularly if this distance increases up to and beyond the distance of the intensity maxima in the respective direction. Nevertheless, the partial area of the sample directly around the center point is scanned and imaged with a high yield of luminescence light.

The embodiment of the method according to the present invention described at last may be realized in practice in that the scan area is scanned along a spiral course around the center point.

In all embodiments of the method according to the invention, it is often suitable, prior to scanning the partial area of the sample to scanned, to image the structure marked with the luminescence markers in another way to determine the partial area of the sample to be scanned. As a rule, the partial area of the sample to be scanned or scan area is a partial area of interest of the sample in which particular details of the structure are present or in which particular developments of the structure occur during a biological process. This primary imaging may take place under local or large-area excitation of the luminescence markers for emission of fluorescence light and without using the light that has an effect on the emission of luminescence light.

Prior to scanning the scan area, a larger area of the sample may be scanned with an at least by 50% reduced intensity of the light that has an effect on the emission of luminescence light and/or at an by at least 50% increased scanning speed to determine the position of the partial area to be scanned in the sample. In this primary scanning, all points of the larger area of the sample are subjected to the high intensity of the light in the area of the intensity maxima. This intensity, however, is purposefully reduced and/or only acts upon the luminescence markers over a shorter period of time.

In one embodiment, another scanner is used for scanning the larger area of the sample than for scanning the scan area.

In using different scanners for scanning the larger area of the sample to determine the scan area and for afterwards scanning the scan area, scanners may be used which are particularly suited for scanning the strongly limited, i.e. small scan area. Due to the small dimensions of the scan area, these scanners may be scanners which do not allow for larger movements of the light intensity distribution with the zero point with regard to the sample, which, however, realize the possible movements very quickly and/or precisely. Thus, the scan area can be scanned at a high repetition rate to, for example, monitor quick changes in the structure of interest of the sample in the scan area.

Particularly, a sample stage or sample holder for the sample may be moved in at least one direction with regard to an objective by which the light is directed onto the sample, whereas for scanning the scan area in at least one direction, an electro-optical scanner, an acousto-optical deflector or a galvo scanner or galvo mirror, i.e. a deflecting mirror with a galvanometric drive, is used. The scanner for the scan area may be combined with an additional electro-optical or acousto-optical modulator as a phase shifter for shifting the zero point of the light intensity distribution.

As already mentioned, the light that has an effect on the emission of luminescence light by the luminescence markers may particularly be luminescence inhibiting light which inhibits the emission of luminescence light by the luminescence markers outside the zero point. For example, the luminescence inhibiting light transfers or switches the luminescence markers in form of switchable proteins into a dark state in which they are not excitable for emission of luminescence light. The luminescence inhibiting light may particularly be directed onto the sample in combination with excitation light which excites the luminescence markers for emission of luminescence light and which has an intensity distribution with an intensity maximum in the area of the zero point of the luminescence inhibiting light. Except of the tight limits to the scan area or of the scanning with increasing distance to the center point of the scan area, this corresponds to the usual procedure in STED, RESOLFT or GSD fluorescence light microscopy.

In an embodiment of the method according to the invention, the concept known from WO 2014/108455 A1, i.e. carrying carry out STED fluorescence microscopy with switchable luminescence markers to protect the luminescence markers against the high intensities in the area of the intensity maxima of the stimulation light by switching them into an inactive state, is applied in a modified form. Particularly, additional switching off light is directed onto the sample with such an intensity distribution that it switches the switchable luminescence markers into an inactive state in a partial area of the sample neighboring the scan area prior to scanning the scan area with the zero point. This neighboring area is neighboring the scan area in the at least one direction in which the intensity maxima are neighboring the zero point of the stimulation light in the sample. In this way, the luminescence markers are switched into the inactive state there, where the intensity maxima of the stimulation light are located and where, without this protection measure, the luminescence markers would be bleached by the high intensities of the stimulation light in scanning the scan area. In that bleaching of the luminescence markers outside the scan area is inhibited in this embodiment of the method according to the invention, it may successively be carried out for directly neighboring or even overlapping scan areas. In other words, the sample may be scanned with the scan area, wherein the scan area, in all or at least in selected positions in the sample, is scanned with the zero point.

The intensity distribution of the switch off light in the respective neighboring area to be scanned afterwards may comprise a local intensity minimum in the scan area formed by destructive interference, in which it does at least essentially not switch off the luminescence markers, i.e. in which it at least essentially leaves the luminescence markers in their active state in which they are excitable by the excitation light. Depending on the selection of the switchable luminescence markers, this active state may require or at least make it suitable that, prior to or temporarily overlapping with directing the light to the sample, switch on light is directed onto the respective partial area of the sample to be scanned, which switches on the switchable luminescence markers into their active state.

When being switched on and/or off, switchable luminescence markers often emit luminescence light. This luminescence light may be registered and evaluated. The goal of this evaluation may, for example, be a decision whether the scan area delimited by the respective neighboring area is scanned with the zero point at all, or whether the scan area is only subjected to excitation light as a whole while luminescence light emitted then is registered confocally, or whether the scan area is not at all subjected to excitation light as the low intensity of the luminescence light registered while switching on and/or off indicates that there is no relevant concentration of luminescence markers. Further, the evaluation may have the goal to determine under which conditions directing the stimulation light onto the sample in each position of the zero point in the scan area delimited by the neighboring partial area and the registration of the luminescence light emitted out of the area of the zero point may suitably be stopped. For example, an upper and/or a lower threshold value for carrying out a RESCue method in the respective scan area may be set depending on the result of the evaluation.

In an embodiment of the method according to the invention, luminescence light emitted out of the area of the zero point is registered with a point detector whose position with regard to the sample is not varied during scan area. This means that the movement of the zero point of the light intensity distribution of the light that has an effect on the emission of luminescence light by the luminescence markers is not considered in registering the luminescence light with the point detector. This is possible, because the dimensions of the scan area are, as a rule, clearly smaller than the detection area of a point detector with regard to the sample. This even and particularly applies to a point detector confocally arranged with regard to the center point of the scan area. The luminescence light out of the entire scan area will reach such a point detector, because the dimensions of the scan area are, as a rule, smaller than the diffraction barrier at the wavelength of the luminescence light. The spatially point sensor being fixed means that the zero point, for scanning the scan area, is only moved by deflecting the light that has an effect on the emission of fluorescence light by the fluorescence markers. Even any excitation light needs not to be shifted together with the light that has an effect on the emission of luminescence light by the luminescence markers as its intensity maximum typically also covers the entire scan area.

As also already mentioned, the light that has an effect on the emission of luminescence light by the luminescence markers may alternatively be luminescence enabling light which enables the emission of luminescence light by the luminescence markers outside the zero point. This includes the option that this light is luminescence excitation light and the only light that is directed onto the sample. This also includes the option that the light is luminescence activation light which transfers the luminescence markers out of a dark state into a state excitable for luminescence, i.e. activates the luminescence markers. The light that has an effect on the emission of luminescence light by the luminescence markers may also have both functions, i.e. activating and exciting, and may have two components of different wavelengths for this purpose. If then a partial area of the sample is scanned with the zero point of the intensity distribution of the light that has an effect on the emission of luminescence light by the luminescence markers, this scan area is kept small to subject the luminescence markers located in the partial area not at all or at least as little as possible to the high light intensities in the area of the intensity maxima neighboring the zero point. Registering the luminescence light emitted by the luminescence markers in the sample in this embodiment of the method may be carried out with a camera, and the evaluation typically includes deconvolving the registered intensity distributions with regard to the actual position of the zero point in the sample and the associated variations of the intensity distribution of the luminescence light emitted out of the sample and registered with the camera.

The drawback of the method according to the present invention that the each scanned and thus imaged partial area of the sample remains very small may at least partially be compensated for in that the sample is simultaneously scanned in several partial areas. Here, particularly, a grid of zero points of the light that has an effect on the emission of luminescence light by the luminescence markers may be used. Even then, the grid of zero points is not shifted so that the entire sample is imaged, i.e. over the full distances of the zero points in the grid. Instead, the individual partial areas in which the sample is scanned remain separated from each other even in this embodiment of the method according to the present invention. Only then the reduction of the danger of bleaching the luminescence markers in the scanned partial area is achieved without further measures like switching off an actually not scanned part of the luminescence markers in the sample to protect them against the bleaching effect of the high light intensities. It will be clear to those skilled in the art that, in case of switchable luminescence markers being used in this embodiment of the invention, the switchable luminescence markers will only be in their fluorescent state in the respective scan areas, and that the sample may additionally be scanned with the scan areas and thus be imaged completely.

If several copies of an object of interest are arranged each overlapping with one or several scan areas, a partial image of this object is obtained by scanning each scan area. If these partial images are statistically distributed over the object and if their number is sufficiently high, a full image of the entire object of interest may be reconstructed from the partial images. It is clear that this reconstruction requires that the several copies of the object of interest are at least essentially identical. For assigning the partial images to particular points of the object of interest, the copies of the object of interest in the sample may additionally be imaged in another way to determine their position and orientation with regard to the scan areas. The object of interest arranged in several copies in the sample may, for example, be a molecule or a virus or the like. Further, in this embodiment of the method according to the invention the plurality of copies of the object of interest may be subjected to varying surrounding conditions to register the reactions of the object of interest to these varying conditions. For this purpose, the individual scan areas are scanned with the respective zero point during and/or before and after the change in the surrounding conditions. The sequence of the successive scans of the scan areas with the respective zero point may be very high so that even fast changes in the object of interest may be registered.

A scanning luminescence light microscope according to the invention comprises a light source for the light that has an effect on the emission of luminescence light by the luminescence markers, a light shaper which directs the light onto the sample with an intensity distribution having a zero point and intensity maxima neighboring the zero point, a scanner to scan the partial area of the sample to be scanned with the zero point, a detector registering the luminescence light emitted out of the area of the zero point, and a controller for carrying out one of the methods according to the invention.

The detector may be a point detector, wherein the position of the point detector may be fixed with regard to the sample during scanning the scan area. This means that the detector may detect the luminescence light emitted out of the sample without descanning the luminescence light, because the scan area, as a rule, will have dimensions well below the diffraction barrier. Then, a further scanner may be provided which differs from the scanner for scanning the scan area with the zero point and which is configured to scan, in at least one direction, a larger area of the sample.

The scanner for scanning the larger area of the sample in at least one direction may include a sample holder or stage which is movable with regard to an objective lens of the light shaper, whereas the scanner for scanning the partial area of the sample to be scanned in at least one direction may include an electro-optical scanner, an acousto-optical deflector, a galvo scanner or a galvo mirror.

The detector may, for example, be a point detector which registers the descanned luminescence light emitted out of the sample, or a two-dimensional detector, like a camera, which registers the not descanned luminescence light in a fixed relative position with regard to the sample.

In a scanning luminescence light microscope according to the present invention for carrying out an STED method according to the present invention, the light provided by the light source is stimulation light, and there is a further light source providing excitation light, wherein the light shaper directs the excitation light onto the sample with an intensity distribution which has a maximum in the area of the zero point of the luminescence inhibiting light.

For carrying out the method according to the invention which makes use of switchable luminescence markers, an additional switch off light source for switch off light is to be provided in the scanning luminescence light microscope, wherein the light shaper directs the switch off light onto the sample with such an intensity distribution that it switches off the switchable luminescence markers into an inactive state in a partial area of the sample neighboring the partial area to be scanned. The neighboring area is neighboring the scan area in the at least one direction in which the intensity maxima are neighboring the zero point of the stimulation light in the sample. Additionally, a switch on light source for switch on light may be provided, which switches the switchable luminescence markers into their active state, wherein the light shaper, prior to or temporarily overlapping with the switch off light, directs the switch on light onto the sample in a partial area including the scan area.

In experiments for testing the method according to the invention, an increase in the yield of photons from the luminescence markers in the sample by a factor >100 has been achieved. This means that one hundred times more images may be taken from a changing structure of interest in the sample to record its changes. Additionally, the time needed for each individual image is smaller, as continuously more photons per time unit are emitted by the luminescence markers in the sample.

Figure 1:
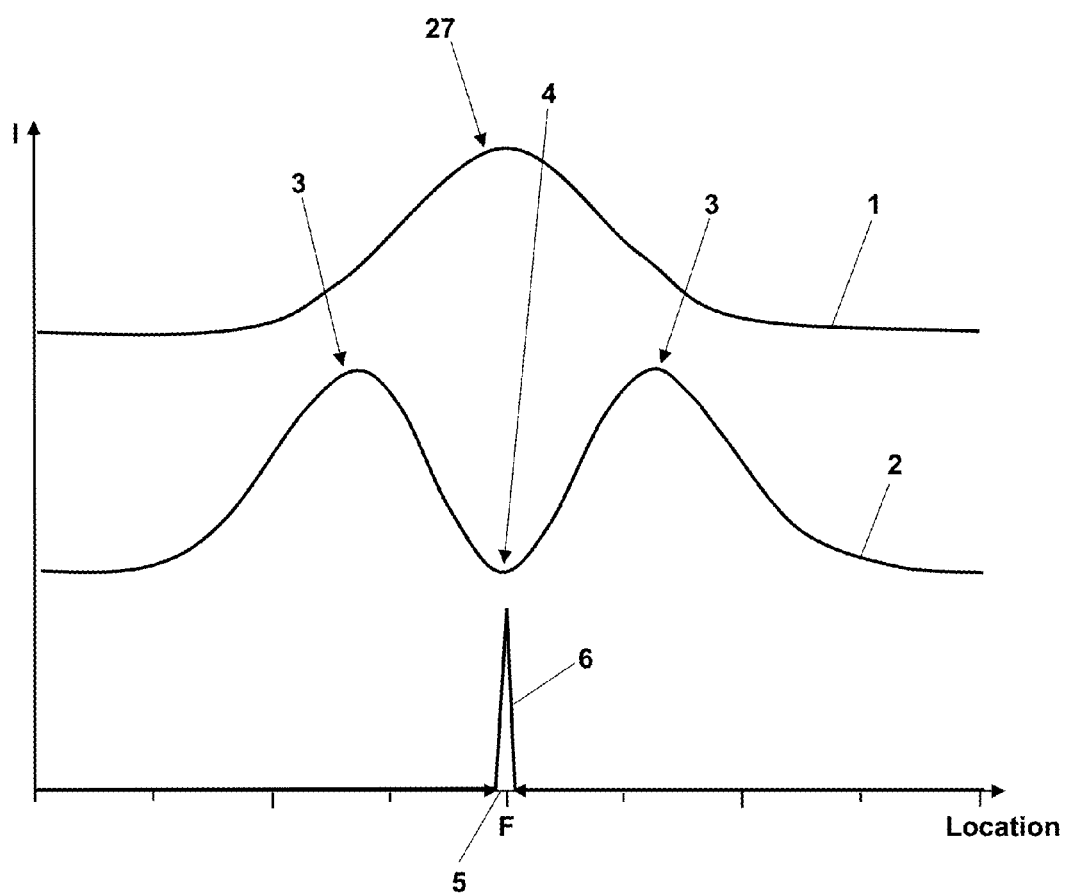

Now referring now in greater detail to the drawings, FIG. 1, at its top, depicts a section through an intensity distribution of excitation light 1. The excitation light 1 has an intensity maximum 27 of a maximum intensity I at a geometric focal point F. However, the intensity I is distributed over an area with dimensions extending far beyond the focal point F in all directions. The diameter of this area corresponds to the diffraction barrier at the wavelength lambda of the excitation light 1 and the numerical aperture NA of an objective lens used for focusing the excitation light 1 into the focal point F according to lambda/NA. To limit the effective excitation of the luminescence markers in the sample to a smaller area than the area over which the intensity distribution of the excitation light 1 extends, fluorescence inhibiting light 2 is additionally directed onto the sample which has a zero point 4 and intensity maxima 3 neighboring the zero point 4. The luminescence inhibiting light 2 inhibits the emission of luminescence light by the fluorescence markers excited by the excitation light 1 in that the fluorescence markers are, for example, de-excited again by means of stimulated emission. Everywhere outside the area 5 of the zero point 4 of the fluorescence inhibiting light 2, the intensity I of the fluorescence inhibiting light 2 is so high that this de-excitation is complete, i.e. that the luminescence markers located there do not emit any fluorescence light. Vice versa, the term "zero point 4" refers to the entire area 5 within which the intensity I of the fluorescence inhibiting light 2 remains so small that it does at least not completely inhibit the emission of fluorescence light by the fluorescence markers located here. At the bottom, FIG. 1 shows the spatial distribution of the effective fluorescence excitation 6. This effective fluorescence excitation 6 is limited to the area 5 of the zero point 4. If a sample is scanned with the zero point 4, fluorescence light emitted out of the sample always comes out of the area 5 and may thus be assigned to the location of the area 5 within the sample.

When the zero point 4 during scanning a sample gets closer to a structure of interest marked with fluorescence dye, i.e. with the fluorescence markers, the fluorescence markers first get into the area of the intensity maxima 3 and the superimposed intensities of the excitation light 1 before they get into the area 5 of the zero point 4. Particularly during scanning the sample line by line, the fluorescence markers are repeatedly subjected to high light intensities before they get into the area 5 and fluorescence light emitted by them is registered for the first time. This may result in that the fluorescence markers are already bleached before they first get into the area 5. Due to this effect, repeatedly scanning the same sample to, for example, monitor temporal changes of the structure of interest marked with the fluorescence markers in the sample is often impossible.

Figure 2:
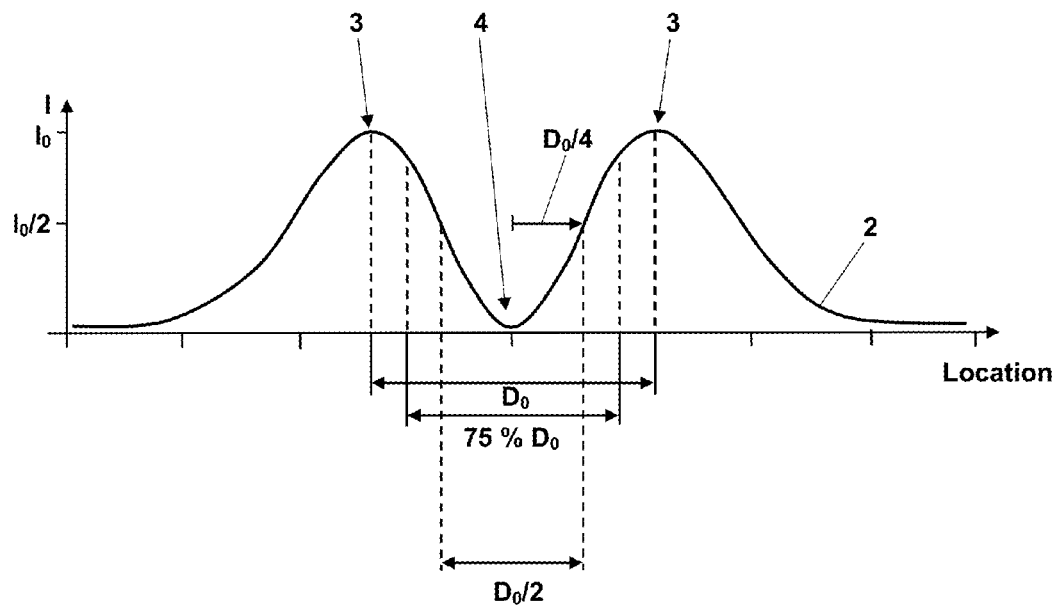
FIG. 2 shows, for the intensity distribution of the fluorescence inhibiting light according to FIG. 1, dimensions of a scan area of a sample to be scanned with the intensity distributions according to FIG. 1 in a method according to the invention.

If, however, the scan area of the sample scanned with the zero point 4 is delimited to not more than ¾ or 75% of a distance Do of the intensity maxima 3 as it is depicted in FIG. 2, the average stress of the fluorescence markers in the scan area caused by the high intensities of the fluorescence inhibiting light 2 in the area of the intensity maxima, particularly in combination with the intensity of the excitation light 1 according to FIG. 1, is already reduced. This stress is further reduced, if the dimensions of the scan area are limited to not more than half the distance $D_0$ of the intensity maxima 3. With limiting the dimensions to less than $D_0/2$, no point of the scan area gets into the peak regions of the intensity maxima 3 when scanning the scan area. If the dimensions of the scan area are limited to $D_0/4$, the maximum intensity of the fluorescence inhibiting light 2 to which the sample is subjected to within the scan area is reduced to about $I_0/2$, wherein $I_0$ is the maximum intensity of the fluorescence inhibiting light 2 in the intensity maxima 3.

Figure 3:
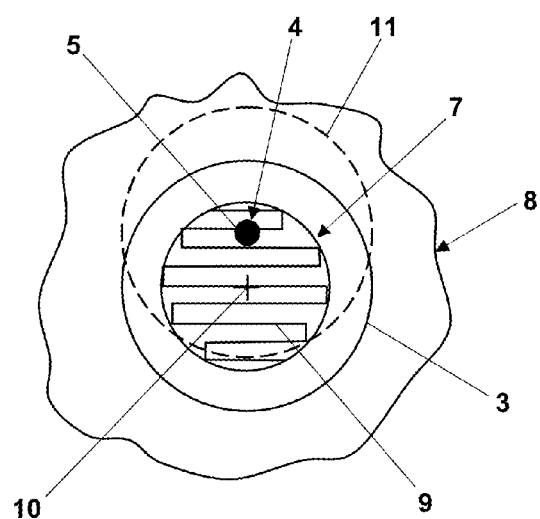
FIG. 3 is a schematic drawing of a scan area of a sample to be scanned in a top view, wherein scanning takes place along a meander-shaped course.

FIG. 3 illustrates scanning a scan area 7 of a sample 3 which is only in part depicted here with the area 5 of the zero point 4 along a course 8 which is meander-shaped here. The partial area 7 to be scanned is depicted within the intensity maxima 3, wherein the positions of these intensity maxima 3 correspond to an alignment of the zero point 4 to a center point 10 of the scan area 7. Correspondingly, the intensity maxima or more precisely the here ring-shaped intensity maximum 3 extending around the position of the zero point 4 highlighted in FIG. 3 and indicated with a dashed line 11 still overlaps with the scan area 7. This overlap, however, may be avoided by further limiting the dimensions of the scan area 7 to less than $D_0/2$. However, even by means of the limitation of the dimensions of the partial area 7 to about $2D_0/3$ as depicted here, a considerable reduction of the average load of the fluorescence markers in the scan area 7 by the fluorescence inhibiting light 2 is achieved.

Figure 4:
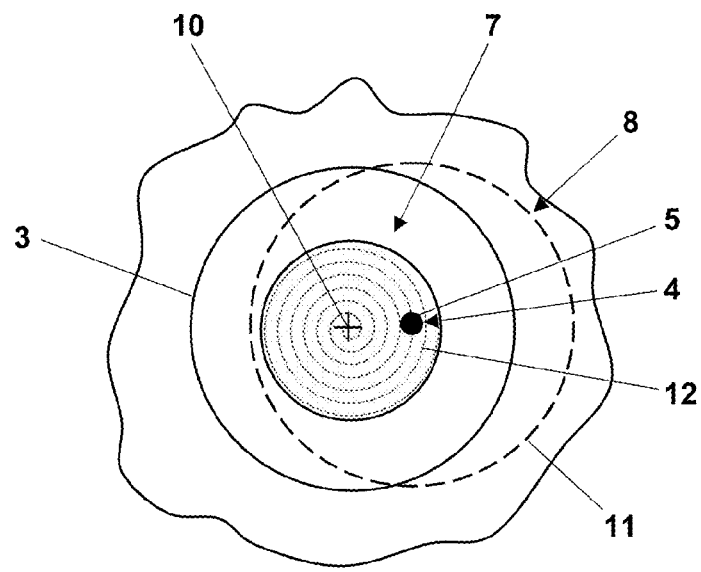
FIG. 4 is a schematic drawing of a scan area of a sample to be scanned in a top view, wherein scanning takes place along a spiral-shaped course.

FIG. 4 illustrates a scan area 7 of the sample 8, which is reduced to $D_0/2$. Here, the course of the ring-shaped intensity maximum 3 indicated with the dashed line 11 does no longer reach the partial area 7 in any position of the zero point 4 within the scan area 7. Further, FIG. 4 shows a spiral course 12 along which the scan area 7 is scanned starting from the center point 10. Independent on the shape of the course along which the zero point 4 is moved when scanning the scan area 7, the fluorescence light emitted out of the sample 8 and registered is assigned to the respective location of the zero point 4 within the sample 3.

Figure 5:
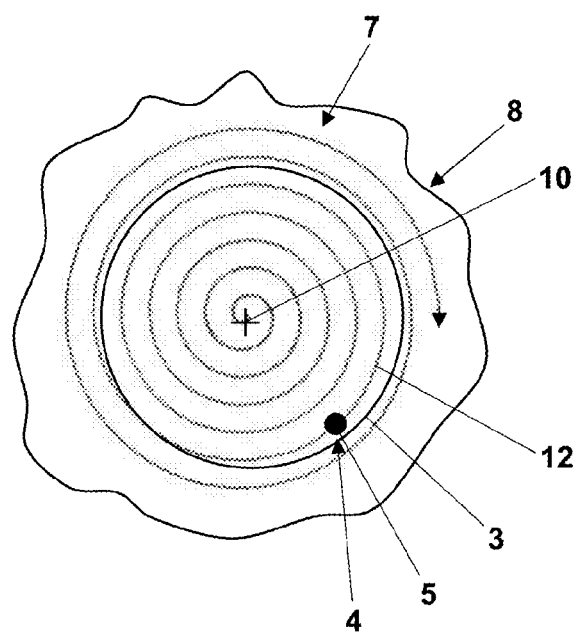
FIG. 5 is a schematic drawing of a scan area of a sample to be scanned in a top view in another method according to the invention, wherein scanning also takes place along a spiral-shaped course.

The embodiment of the invention illustrated in FIG. 5 differs from those embodiments illustrated in FIGS. 3 and 4 in that the scan area 7 is no longer limited to a fraction of what is encircled by the ring-shaped maximum 3 around the center point 10. Instead, along a spiral course 12 a partial area 8 of the sample is scanned whose diameter is larger than that one of the ring-shaped maximum 3 around the center point 10. Here, the prior subjection to the fluorescence inhibiting light 2 of parts of the scan area 7 which are only later crossed by the spiral course 12 steadily increases. In the parts close to the center point 10, the prior loads by the fluorescence inhibiting light 2 are, however, minimal. If the center point 2 of the scan area 7 is directed to a particularly interesting point of the sample 8, a maximum yield of fluorescence light from the sample 8 is achieved here which decreases with increasing distance to the center point 10 but which remains sufficient for imaging the surroundings of the particularly interesting point of the sample 8.

FIG. 6 illustrates a scanning fluorescence light microscope 13 which is particularly suited for carrying out a method according to the present invention. The scanning fluorescence light microscope 13 comprises a light source 14 providing the fluorescence inhibiting light 2 whose cross section is widened by means of a widening optic 15 and whose wave fronts across its cross section are modulated by means of a phase plate 16 in such a way that the zero point 4 and the neighboring intensity maxima 3 according to FIGS. 1 and 2 are formed around the respective focus point F when the fluorescence inhibiting light 2 is focused into the sample 8 by means of an objective lens 45. A further light source 17 with a further widening optic 18 is providing the excitation light 1. By means of a dichroitic mirror 19, the excitation light 1 and the fluorescence inhibiting light 2 are combined such that the excitation light 1 has its intensity maximum 27 according to FIG. 1 in the area 5 of the zero point 4 of the fluorescence inhibiting light 2. The fluorescence light 20 emitted out of the area of the zero point of the fluorescence inhibiting light 2 is separated by means of a dichroitic mirror 26, registered with a point detector 21 and assigned to the respective location of the zero point 4 within the sample 8. Scanners 22 and 23 are provided for two orthogonal scanning directions, and they are operated in combination for scanning the respective scan area in the sample 8 with the zero point of the fluorescence inhibiting light 2. The scanners 22 and 23 only have an influence on the direction of the excitation light 1 and the fluorescence inhibiting light 2; they may even only be arranged in the beam path of the fluorescence inhibiting light 2. As the scan area 7 of the sample 8 has dimensions below the diffraction barrier, the fluorescence light 20 emitted out of the area of the zero point of the fluorescence inhibiting light 2 within the scan area in the sample 8 always gets into the point detector 21 even with a spatially fixed arrangement of the point detector 21 with regard to the sample 3, i.e. despite the shifting of the zero point by means of the scanners 22 and 23. This is because the scan area 7 has dimensions below the diffraction barrier. For scanning the sample 8 beyond the scan area 7 to, for example, at first determine the position of a suitable scan area, further scanners are provided in the area of the sample holder 24 which are here only indicated by corresponding shifting symbols 25.

Up to here, it has not yet been explicitly stated that the zero point 4 of the intensity distribution of the fluorescence inhibiting light 2 may also be delimited by neighboring intensity maxima 3 in a z-direction in which the fluorescence inhibiting light 2 is directed onto the sample to increase the spatial resolution in imaging the structure of interest in the sample 8 also in this z-direction. Correspondingly, the scan area 7 is then also to be limited in this z-direction to not more than 75%, preferably less than 50% of the distance of the intensity maxima of the light in the z-direction or also to be scanned in the z-direction starting at its center point 10 and with increasing distance to the center point 10. An increased spatial resolution in imaging the sample in z-direction may also be achieved by other measures like, for example, a 4PI arrangement or a 2 photon excitation of the fluorescence markers for emitting the fluorescence light or other measures known in the field of fluorescence microscopy. It also generally applies that the methods described here may be supplemented with other measures known in the field of fluorescence microscopy. Applying the fluorescence inhibiting light 2 and/or the excitation light 1 in pulses, a simultaneous continuous application of the excitation light 1 or the fluorescence inhibiting light 2, a gated registration of the fluorescence light in a defined temporal gate after the respective pulses and so on belong to these measures.

The confocal image according to FIG. 7 (a) has been taken of a sample in which a structure of interest has been marked with the luminescence marker Nukleoporine gp210. The confocal image provides an overview over the structure of interest. From this overview, separate scan areas have been selected in which STED images have been taken according to the method of the present invention. These scan areas are smaller than the focal area of the excitation light. In the scan areas, the structure of interest is imaged both at a high spatial resolution and at a high yield of fluorescence light. For imaging the partial image of the sample depicted in FIG. 7 (b) and presenting the scan areas, excitation light at a wavelength of 635 nm and at a power of 5 µW has been directed to the sample in pulses at a repetition rate of 20 MHz. STED light at a wavelength of 775 nm has been directed to the sample in synchronized pulses at a pulse length of 1.2 ns at a power of 150 mW. The excitation light and the STED light have been focused into the sample by means of an 1.4 NA oil inversion objective lens. The fluorescence light has been focused by means of the oil inversion objective lens and a further lens onto a point detector.

FIG. 8 illustrates the bleaching behavior of dyed nuclear pore protein complexes depending on the dimensions of the scan area in STED scanning fluorescence light microscopy. $\tau\frac{1}{2}$ indicates the number of images which may be taken before the fluorescence signal drops to half of the starting value due to bleaching. $\tau\frac{1}{2}$ is plotted over the dimensions of the scan area in nanometer. The STED power was 160 mW, the excitation power 2 µW. Otherwise, the STED conditions corresponded to those according to FIG. 7. With dimensions of the scan area of $100\times100$ nm$^2$, bleaching is reduced by a factor of 100 as compared to dimensions of $800\times800$ nm$^2$. Correspondingly, 100 times more images may be taken of the same scan area to, for example, monitor a dynamic process in the sample.

The scanning fluorescence microscope 13 according to FIG. 9 comprises the following differences with regard to the scanning fluorescence microscope depicted in FIG. 6. As viewed from the sample 8, the point detector 21 is arranged behind the scanners 22 and 23 so that the scanners descan the fluorescence light 20 coming from the sample 3 towards the detector 21. Here, the scanners 22 and 23 are provided both for scanning the scan area to be scanned with the zero point of the fluorescence inhibiting light 2 and for generally arranging and shifting the scan area in the sample 8. FIG. 9 also shows a detector 28 for fluorescence light arranged upstream to the scanners 22 and 23 as viewed from the sample 8. This, however, is no point detector but a camera 29, i.e. a two-dimensional detector. This detector 28 may be provided in addition to the point detector 21 or instead of the point detector 21, wherein a dichroitic mirror 30 deflecting the fluorescence light 20 towards the detector 28 is either temporarily or permanently arranged between the objective lens 45 and the scanners 22 and 23.

Further, there is a switch off light source 31 to which a widening optic 32 is assigned in the scanning fluorescence microscope 13 according to FIG. 9 to provide switch off light 34 prior to scanning the respective scan area with the zero point of the fluorescence inhibiting light 2. The switch off light 34 is coupled in by means of a dichroitic mirror 43, and its intensity distribution in the sample 8 is formed by beam shaper 33 such that it switches switchable luminescence markers located in the sample 8 in a partial area of the sample 8 neighboring the partial area to be scanned into an inactive state. In this inactive state, the switchable luminescence markers in the sample 8 are not excitable for the emission of fluorescence light 20 by means of the excitation light 1. Correspondingly, there is no relevant danger of bleaching due to the fluorescence inhibiting light 2 in form of stimulation light for the luminescence markers in the area neighboring the scan area. Thus, with the scanning fluorescence microscope 13 according to FIG. 9, it is possible to scan a further scan area of the sample 8 which is neighboring an already scanned scan area of the sample 8 with the zero point of the fluorescence inhibiting light 2 and to register fluorescence light 20 emitted out of the sample 3 because the luminescence markers located in the further scan area have not been bleached by previously scanning the neighboring scan area as they have been in their inactive state protecting them against bleaching.

To be able to excite the luminescence markers in the neighboring scan area with the excitation light 1 for emission of fluorescence light 20, they have to be in their active state. To achieve this, one may wait for a spontaneous return of the luminescence markers out of their inactive state into their active state. The scanning fluorescence microscope 13 according to FIG. 9, however, also comprises an additional switch on light source 35 with a widening optic 36 providing switch on light 37 and directing it onto the sample 8 via a dichroitic mirror 44. By means of the switch on light the luminescence markers in the next scan area are at first switched into their active state. The partial area of the sample 8 covered by the switch on light 37 may be larger than the scan area to be scanned next, as afterwards, by means of the switch off light 34, the luminescence markers outside the scan area to be scanned next are transferred into their inactive state. Thus, the sample 8 may be scanned with the scanning fluorescence microscope 13 in two steps, i.e. in big steps with the scan area and in small steps with the zero point of the fluorescence inhibiting light 2 within each location of the scan area.

In switching on and/or switching off the luminescence markers in the sample 8 with the switch on light 37 or the switch off light 34, various switchable luminescence markers are also excited for the emission of fluorescence light 20. This fluorescence light 20 thus already provides information about the concentration of the luminescence markers in the respective partial area of the sample 8. This information may correspondingly be evaluated and used for a decision on whether there is any value in scanning the next scan area with the zero point of the fluorescence inhibiting light 2 or not. If there is no value, such a scanning will also not be executed to not unnecessarily subject the sample 8 to the fluorescence inhibiting light 2. Additionally, the fluorescence light registered during switching on and switching off the luminescence markers may be used to set an upper and/or lower threshold for the fluorescence light registered at the respective location of the zero point of the fluorescence inhibiting light 2 in the scan area to limit the subjection of the sample 8 to the fluorescence inhibiting light 2 and the excitation light 1 as early as suitable according to a RESCue method.

Last but not least, FIG. 9 depicts a controller 38 for the light sources 14 and 17, the switch on light source 35, the switch off light source 31 and the scanners 22 and 23 of the scanning fluorescence microscope 13 to control them for carrying out the method according to the invention.

FIG. 10 depicts a scan area 7 and the intensity maximum 3 of the fluorescence inhibiting light encircling this partial area 7, the zero point of the fluorescence inhibiting light being in the center point 10 of the scan area 7. Additionally, a ring-shaped neighboring partial area 39 is depicted in FIG. 10, within which the sample 8, prior to scanning the scan area 7 is subjected to the switch off light 34 to transfer the switchable fluorescence markers located here into their inactive state. The partial area 39 leaves out the scan area 7, i.e. the intensity of the switch off light 34 is zero or at least so small in the scan area 7 that it is not sufficient for switching off the luminescence markers within the period of time for which the switch off light 34 is directed to the sample 8. To ensure that the switchable luminescence markers, at least in the scan area 7, are in their active state, the switch on light 37 is directed onto the sample 8 in a circular-shaped partial area 40 which includes the scan area 7 prior to or temporarily overlapping with the switch off light 34.

FIG. 11 illustrates how the sample 8 may be scanned with the scan area 7. Here, FIG. 11 (*a*) shows several consecutive positions of the circular scan area 7 according to FIG. 10 in the sample 8; and for one of these positions of the scan area 7 the course 9 along which a square area of the sample 8 is scanned is depicted within the partial area 7. FIG. 11 (*b*) shows how the sample 8 may be completely covered with such square partial areas 41 and thus be imaged completely.

FIG. 12 illustrates another way of scanning the sample 8 with the scan area 7. Here, the consecutive positions of the circular scan area 7 are arranged in a hexagonal arrangement within the sample 8. The course 9 along which the partial area 7 is scanned with the zero point of the luminescence inhibiting light in each of its positions extends over a regular hexagon. FIG. 12 (*b*) shows how the entire sample 8 may be covered and thus imaged with these regular hexagons 42.

FIG. 13 is a block diagram of a method according to the present invention starting with a step 46 of determining the scan area 7 both with regard to its dimensions and its location in the sample 8. In a next step 47 the scan area 7 is scanned with the zero point 4 of the intensity distribution of the fluorescence inhibiting light 2. In a parallel step 48, the fluorescence light emitted out of the sample is registered. In a step 49 the fluorescence light registered in step 48 is assigned to the present location of the zero point 4 in step 47. This implies that in step 48 the fluorescence light emitted out of the sample 8 is registered at a temporal resolution, and that in step 47 the scan area 7 is scanned with the zero point 4 at a temporal resolution so that a particular amount of fluorescence light registered in step 48 can be assigned to a particular position of the zero point 4 in the scanning area 7. By means of the steps 47 to 49 the scanning area 7 is scanned and imaged once. This imaging may be repeated to, for example, monitor changes to a structure of interest marked with the fluorescence markers in the scan area 7.

The embodiment of the method of the invention depicted in FIG. 14 starts with the step 46 of determining the scan area 7. In a following step 50, the fluorescence markers in an area including the scan area 7 are switched on into an active state. This implies that the fluorescence markers are switchable markers which may by switched on by switch on light 37, for example. In a next step 51 the fluorescence markers outside the scan area 7 are switched off into an inactive state. This may be done by switch off light 34. In the inactive state, the fluorescence markers are protected against bleaching by high light intensities of the fluorescence inhibiting light 2. Next, in the step 47, the scan area 7 is scanned with the zero point 4 of the intensity distribution of the fluorescence inhibiting light. Afterwards, step 46 is repeated. In this repetition of step 46, the scan area 7 may by placed at a position neighboring the previous position of the scan area 7. Although the fluorescence markers have been subjected to the high intensities of the fluorescence inhibiting light here, they are not bleached here because they have been in their inactive state. Thus, they may now be measured. The loop including the steps 46, 50, 51 and 47 is then repeated until all areas of interest in the sample are scanned with the scan area 7 and thus imaged.

Many variations and modifications may be made to the preferred embodiments of the invention without departing substantially from the spirit and principles of the invention. All such modifications and variations are intended to be included herein within the scope of the present invention, as defined by the following claims.

We claim:

1. A method of high resolution imaging a structure in a sample, the structure being marked with luminescence markers, the method comprising
   directing light that has an effect on the emission of luminescence light by the luminescence markers onto the sample with an intensity distribution which has a zero point and intensity maxima neighboring the zero point in at least one direction and having a distance in the at least one direction;
   scanning a scan area with the zero point, the scan area being a part of the sample;
   while scanning the scan area registering luminescence light emitted out of a local area including the zero point in the sample;
   assigning the registered luminescence light to a respective location of the zero point in the sample; and
   limiting dimensions of the scan area, in the at least one direction in which the intensity maxima are neighboring the zero point in the sample, to not more than 75% of the distance of the intensity maxima in the at least one direction.

2. The method of claim 1, wherein the dimensions of the scan area in the at least one direction in which the intensity maxima are neighboring the zero point in the sample are not larger than 25% of the distance of the intensity maxima in the at least one direction.

3. The method of claim 1, wherein the dimensions of the scan area in the at least one direction in which the intensity maxima are neighboring the zero point in the sample are not larger than a distance over which an intensity of the light in the at least one direction, starting at the zero point, increases up to 25% of the intensity of the light in the neighboring intensity maxima.

4. The method of claim 1, wherein the scan area is repeatedly scanned with the zero point.

5. The method of claim 1, wherein, prior to scanning the scan area, the structure in the sample is images in another way to determine a position of the scan area in the sample.

6. The method of claim 5, wherein, prior to scanning the scan area, a larger partial area of the sample is scanned with the zero point at at least one of
   an at least 50% lower intensity of the light and
   an at least 50% higher scanning speed.

7. The method of claim 5, wherein a scanner is used for scanning the scan area, and wherein another scanner is used for scanning the larger area of the sample.

8. The method of claim 5, wherein a sample holder is moved relative to an objective lens by which the light is directed onto the sample for scanning the larger area of the sample, and wherein at least one of
   an electro-optical scanner,
   an acousto-optical deflector,
   a galvo scanner and
   a galvo mirror
is used for scanning the scan area in the at least one direction.

9. The method of claim 1, wherein the light is luminescence inhibiting light whose wavelength is selected such as to inhibit the emission of luminescence light by the luminescence markers outside the zero point.

10. The method of claim 9, wherein the luminescence inhibiting light is stimulation light whose wavelength is selected such as to inhibit the emission of luminescence light by the luminescence markers outside the zero point by stimulated emission, wherein the stimulation light is directed onto the sample together with excitation light whose wavelength is selected such as to excite the luminescence markers for emission of luminescence light and which has an intensity distribution comprising a maximum in the area of the zero point of the luminescence inhibiting light.

11. The method of claim 10, wherein, prior to scanning the scan area with the zero point, additional switch off light is directed onto the sample with such an intensity distribution that the switch off light, in a neighboring area, switches the luminescence markers into an inactive state, wherein the neighboring area is neighboring the scan area in the at least one direction in which the intensity maxima are neighboring the zero point of the stimulation light in the sample.

12. The method of claim 11, wherein the sample is scanned with the scan area, wherein the scan area in all positions or in selected positions of the scan area in the sample is scanned with the zero point.

13. The method of claim 11, wherein the intensity distribution of the switch off light comprises a local intensity minimum formed by destructive interference in the scan area.

14. The method of claim 11, wherein, prior to or temporarily overlapping with directing the switch off light to the sample, switch on light is directed onto the scan area of the sample that switches the luminescence markers into their active state.

15. The method of claim 14, wherein luminescence light emitted by the switchable luminescence markers upon being switched on or off is registered and evaluated.

16. The method of claim 15, wherein a result of the step of evaluating is at least one of the following:
   whether the scan area delimited by the neighboring area will be scanned with the zero point;
   whether the excitation light will be directed onto the sample in the scan area delimited by the neighboring partial area; and
   under which conditions directing the stimulation light onto the sample in each position of the zero point in the scan area delimited by the neighboring area, and registering the luminescence light emitted out of the area of the zero point will be interrupted.

17. The method of claim 1, wherein the luminescence light emitted out of the area of the zero point is registered with a point sensor whose position with regard to the sample remains unchanged during scanning the scan area.

18. The method of claim 1, wherein several scan areas of the sample are scanned simultaneously.

19. The method of claim 18, wherein several copies of an object of interest are arranged in the sample with an overlap with the several scan areas, wherein an image of the object of interest is composed of partial images of the object which are obtained in scanning the several scan areas.

20. A method of high spatial resolution imaging a structure in a sample, the structure being marked with luminescence markers, the method comprising
   directing light that has an effect on the emission of luminescence light by the luminescence markers onto the sample at an intensity distribution which has a zero point and intensity maxima neighboring the zero point in at least one direction;
   scanning a scan area with the zero point, the scan area being a part of the sample;
   while scanning the scan area registering luminescence light emitted out of a local area including the zero point in the sample; and
   assigning the registered luminescence light to a respective location of the zero point in the sample;

wherein the scan area is scanned with the zero point starting at a center point and with increasing distance to the center point in the at least one direction.

21. The method of claim 20, wherein the scan area is scanned along a spiral course around the center point.

22. A scanning luminescence light microscope comprising
a light source configured to provide light;
a light shaper configured to direct the light onto a sample with an intensity distribution having a zero point and intensity maxima neighboring the zero point;
a scanner configured to scan a scan area with the zero point, the scan area being a partial area of the sample;
a detector configured to register luminescence light emitted out of the area of the zero point; and
a controller programmed with software implementing a method of high resolution imaging a structure in a sample, the structure being marked with luminescence markers, the method comprising
directing light that has an effect on the emission of luminescence light by the luminescence markers onto the sample with an intensity distribution which has a zero point and intensity maxima neighboring the zero point in at least one direction and having a distance in the at least one direction;
scanning a scan area with the zero point, the scan area being a part of the sample;
while scanning the scan area registering luminescence light emitted out of a local area including the zero point in the sample; and
assigning the registered luminescence light to a respective location of the zero point in the sample;
limiting dimensions of the scan area, in the at least one direction in which the intensity maxima are neighboring the zero point in the sample, not more than 75% of the distance of the intensity maxima in the at least one direction, or wherein the scan area is scanned with the zero point starting at a center point and with increasing distance to the center point in the at least one direction.

23. The scanning luminescence light microscope of claim 22 and additionally comprising a further scanner configured to scan a larger area of the sample, wherein the detector is a point detector whose position with regard to the sample is fixed while scanning the scan area.

24. The scanning luminescence light microscope of claim 23, wherein the further scanner comprises a sample holder movable with regard to an objective lens of the light shaper.

25. The scanning luminescence light microscope of claim 22, wherein the scanner comprises at least one of an electro-optical scanner, an acousto-optical deflector, a galvo scanner or a galvo mirror.

26. The scanning luminescence light microscope of claim 23, wherein the light provided by the light source is stimulation light, and wherein the scanning luminescence light microscope further comprises:
a further light source configured to provide excitation light, wherein the light shaper is configured to direct the excitation light onto the sample with an intensity distribution having a maximum in the area of the zero point of the stimulation light, and
a switch off light source configured to provide switch off light, wherein the light shaper is configured to direct the switch off light onto the sample at such an intensity distribution that it switches off switchable luminescence markers in a neighboring partial area into an inactive state, wherein the neighboring partial area is neighboring the scan area in the at least one direction in which the intensity maxima are neighboring the zero point of the stimulation light.

27. The scanning luminescence light microscope of claim 26, additionally comprising a switch on light source configured to provide switch on light which switches the switchable luminescence markers into their active state, wherein the light shaper is configured to direct the switch on light onto the scan area prior to or overlapping with directing the switch off light onto the sample.

* * * * *